United States Patent
Waisman et al.

(10) Patent No.: US 9,895,196 B2
(45) Date of Patent: Feb. 20, 2018

(54) APPARATUS AND METHOD FOR REDUCING LASER BEAM ATTENTUATION IN A LIQUID MEDIUM

(71) Applicant: LUMENIS LTD., Yokneam Ilit (IL)

(72) Inventors: Tal Waisman, Haifa (IL); Arkady Khachaturov, Haifa (IL); Assaf Preiss, Shimshit (IL)

(73) Assignee: LUMENIS LTD., Yokneamilit (IL)

( * ) Notice: Subject to any disclaimer, the term of this patent is extended or adjusted under 35 U.S.C. 154(b) by 0 days.

(21) Appl. No.: 15/615,624

(22) Filed: Jun. 6, 2017

(65) Prior Publication Data

US 2017/0354464 A1 Dec. 14, 2017

Related U.S. Application Data

(60) Provisional application No. 62/347,685, filed on Jun. 9, 2016.

(51) Int. Cl.
*A61B 18/20* (2006.01)
*A61B 17/22* (2006.01)
(Continued)

(52) U.S. Cl.
CPC ............... *A61B 18/20* (2013.01); *A61B 17/22* (2013.01); *A61B 17/22004* (2013.01);
(Continued)

(58) Field of Classification Search
CPC  A61B 2017/00176; A61B 2017/22025; A61B 2017/00172; A61B 2017/22089;
(Continued)

(56) References Cited

U.S. PATENT DOCUMENTS

| | | |
|---|---|---|
| 5,321,715 A | 6/1994 | Trost |
| 5,409,479 A | 4/1995 | Dew et al. |

(Continued)

OTHER PUBLICATIONS

Search Report—Corresponding PCT Application No. PCT/IB17/053333, dated Sep. 19, 2017, 5 pages.

*Primary Examiner* — Scott T Luan
(74) *Attorney, Agent, or Firm* — ISUS Intellectual Property PLL

(57) ABSTRACT

A method of optimizing the irradiation of a target with laser radiation includes selecting and mounting on a laser radiation delivery device either a waveguide or optical fiber type to be used; also, selecting at least the following parameters: selecting the total energy of the at least one train of pulses to be delivered to the target, and selecting the distance from the distal delivery end to the target; then, initiating irradiation of the target for the at least one train of pulses by generating a first laser pulse with sufficient energy ($E^i$) to form a vapor bubble in a liquid medium; allowing the vapor bubble formed to expand an amount sufficient to displace a substantial portion of the liquid medium from the space between the distal delivery end and the target; and, thereafter, after the selected time delay ($T^d$) sufficient for the formed vapor bubble to reach its optimum extent, generating a second laser pulse ($E^p$), the second laser pulse being delivered to the target through the formed vapor bubble.

18 Claims, 12 Drawing Sheets

(51) Int. Cl.
*A61B 18/00* (2006.01)
*A61B 17/00* (2006.01)

(52) U.S. Cl.
CPC ............ *A61B 2017/00017* (2013.01); *A61B 2017/22007* (2013.01); *A61B 2018/00625* (2013.01); *A61B 2018/20554* (2017.05)

(58) Field of Classification Search
CPC ... A61B 18/20; A61B 17/22; A61B 17/22004; A61B 2018/20554; A61B 2017/00017; A61B 2017/22007; A61B 2018/00625
See application file for complete search history.

(56) References Cited

U.S. PATENT DOCUMENTS

| | | | |
|---|---|---|---|
| 5,632,739 A * | 5/1997 | Anderson | A61B 18/24 606/15 |
| 2009/0126235 A1 | 5/2009 | Kobayashi et al. | |
| 2013/0084544 A1 | 4/2013 | Boutoussov et al. | |
| 2016/0015471 A1* | 1/2016 | Piron | A61B 6/5247 600/424 |

* cited by examiner

FIG. 4

| E,j/RR,Hz | 5 | 5 | 5 | 10 | 15 | 20 | 25 | 30 | 35 | 40 | 45 | 50 | 60 | 70 | 80 |
|---|---|---|---|---|---|---|---|---|---|---|---|---|---|---|---|
| 0.2 | 150/26 | 150/26 | 150/26 | 150/26 | 150/26 | 150/26 | 150/26 | 150/26 | 150/26 | 150/26 | 150/26 | 150/26 | 150/27 | 150/28 | 180/29 |
| 0.3 | 140/27 | 140/27 | 140/27 | 140/27 | 140/27 | 140/27 | 140/27 | 140/27 | 140/28 | 140/28 | 140/27 | 140/28 | 140/29 | 140/29 | 140/30 |
| 0.4 | 130/24 | 130/24 | 130/24 | 130/24 | 130/24 | 130/24 | 130/24 | 130/24 | 130/24 | 130/24 | 130/24 | 140/24 | 150/25 | 150/26 | 190/27 |
| 0.5 | 160/23 | 160/23 | 160/23 | 160/23 | 160/23 | 160/23 | 160/23 | 160/23 | 160/23 | 160/23 | 160/23 | 160/24 | 160/24 | 160/25 | 160/26 |
| 0.6 | 180/24 | 180/24 | 180/24 | 180/24 | 180/24 | 200/24 | 200/24 | 200/24 | 200/24 | 200/24 | 200/24 | 200/24 | 180/24 | 180/24 | 180/24 |
| 0.8 | 150/24 | 150/24 | 150/24 | 150/24 | 150/25 | 150/25 |   |   |   |   |   |   |   |   |   |
| 1 | 160/24 | 160/24 | 160/24 | 160/24 | 160/24 | 160/24 |   |   |   |   |   |   |   |   |   |
| 1.4 | 160/24 | 160/24 | 160/24 | 160/24 |   |   |   |   |   |   |   |   |   |   |   |
| 1.4 | 160/24 | 160/24 | 160/24 | 160/24 |   |   |   |   |   |   |   |   |   |   |   |
| 1.5 | 150/24 | 150/24 | 150/24 | 150/24 |   |   |   |   |   |   |   |   |   |   |   |
| 1.6 |   |   |   |   |   |   |   |   |   |   |   |   |   |   |   |
| 1.8 |   |   |   |   |   |   |   |   |   |   |   |   |   |   |   |
| 2 |   |   |   |   |   |   |   |   |   |   |   |   |   |   |   |

SL200

Cell format: $E_1$,J / $T_2$,usec

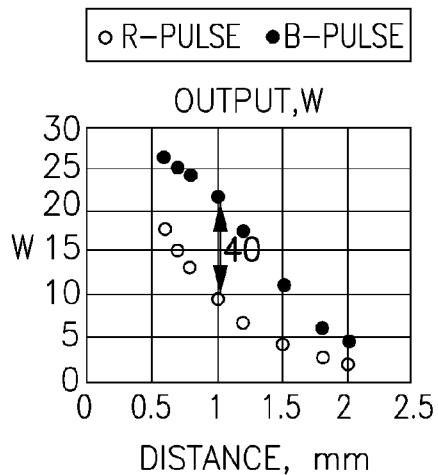
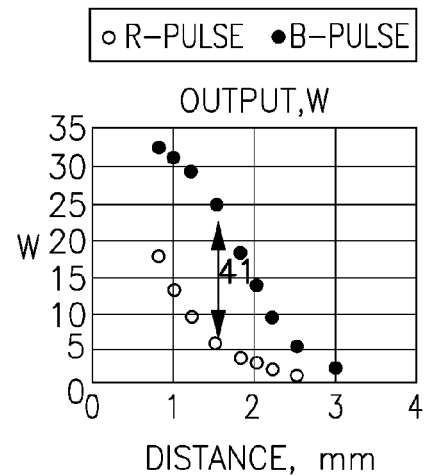
FIG.5A            FIG.5B
THE SAME FIBER OF 365mic CORE SIZE AT THE SAME
WORKING POINT OF 1J, 70HZ OPTIMIZED TO DIFFERENT
DISTANCES (1mm-LEFT AND 1.5mm-RIGHT)
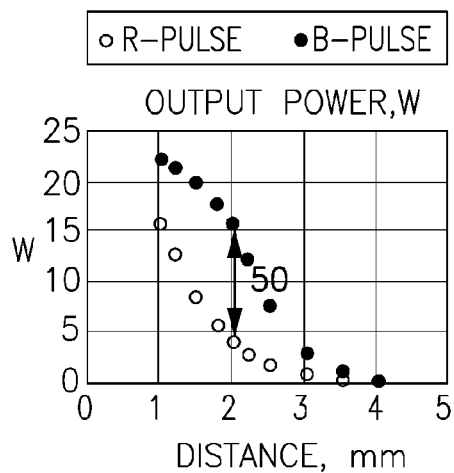
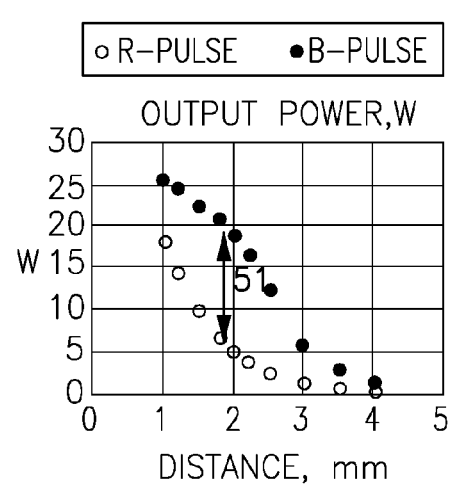
FIG.6A            FIG.6B
THE FIBERS OF DIFFERENT CORE SIZES (365mic –
LEFT 550mic – RIGHT(AT THE SAME WORKING POINT
(2J, 20HZ) OPTIMIZED TO THE SAME DISTANCE OF 2mm

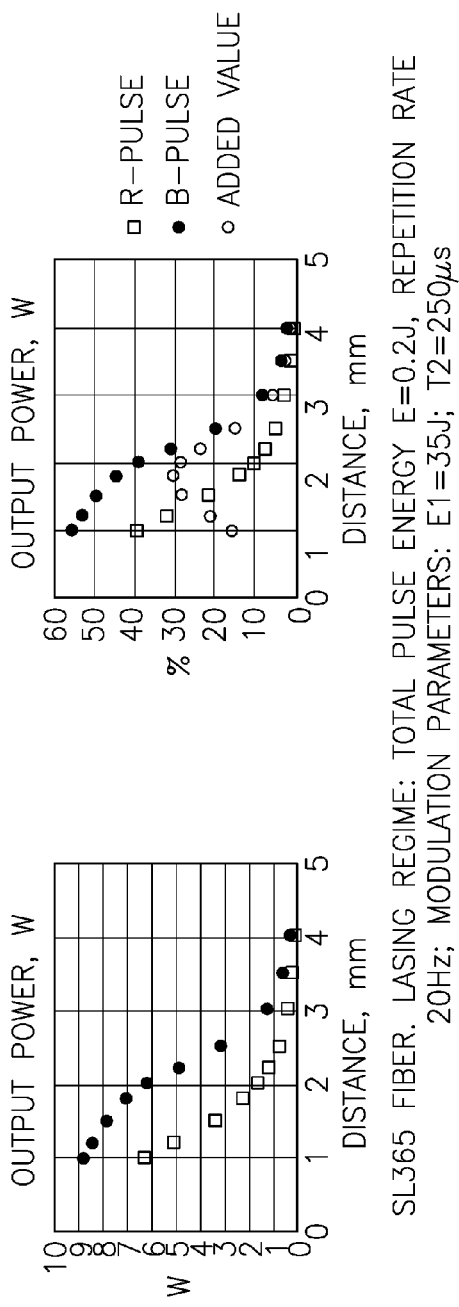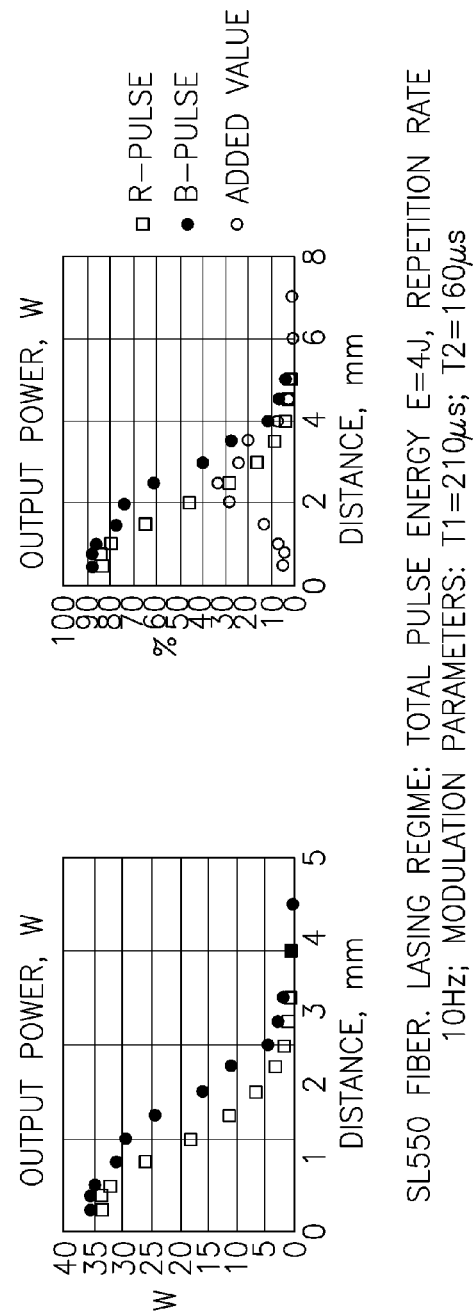

APPARATUS AND METHOD FOR REDUCING LASER BEAM ATTENUATION IN A LIQUID MEDIUM

RELATED APPLICATIONS

The present application is related to and claims priority to U.S. Provisional Application Ser. No. 62/347,685, filed Jun. 9, 2016, the entire contents of which are herein incorporated by reference.

FIELD OF THE PRESENT INVENTION

This invention relates to laser light energy sources and to methods and devices for reducing the attenuation of a laser beam which will transit through a liquid environment to a target tissue.

BACKGROUND OF THE PRESENT INVENTION

Treatments using laser devices have become during the last two decades a common treatment modality in medicine. New laser technologies and delivery systems, followed by price reduction and improved quality of laser delivery systems are only a few driving forces. Some laser treatments are performed under direct irradiation in free, open space, such a laser treatment on the skin surface. However, some treatments are performed with the support of a delivery system such as transmitting the laser beam through an optical fiber or a light guide. In some of these treatments, the treatment site is characterized by a gaseous environment (e.g., during laparoscopic procedures conducted with insufflation gas).

However, some laser treatments are conducted within a liquid environment, such as kidney stone blasting or benign prosthetic hyperplasia ablation, to mention only two. From the optical perspective, the effectiveness of the delivery of energy from a laser beam to a target tissue depends, among other things, on the medium the laser passes through from its point of origin to the target tissue. In general, a liquid medium tends to absorb and scatter light more than a gaseous medium. The liquid medium may include water as a constituent, and water is known to strongly absorb light in general and infrared light wavelengths in particular.

Infrared lasers, such as Thulium, Holmium, Erbium, CO2 lasers and the like, are in common medical use in general surgery, orthopedics, and urological procedures. Since many of these procedures are conducted in the liquid environment within the body, it may be expected that a portion, perhaps even a large portion, of the laser energy emitted from an output tip of an optical fiber or a light guide may be absorbed in the liquid medium before reaching the target tissue.

However, as taught by U.S. Pat. No. 5,321,715 ('715 patent), in some circumstances, laser energy traveling in a liquid medium toward a target tissue will be absorbed, but that absorption may be less than expected. This is due to the so-called "Moses Effect", in which the first component of the emitted energy is absorbed by the liquid and creates a bubble in the liquid medium so that the remaining energy passes through a less-restrictive or absorbing gaseous/vapor medium characterized by a lower optical attenuation.

The '715 patent describes a pulse format to increase the amount of laser energy which will arrive at the target tissue. According to the description, a first short and low energy initiation pulse is generated in order to create a bubble, followed by a higher energy treatment pulse. The second treatment pulse, when it passes through the created and now-formed bubble, experiences a lower absorption rate due to the presence of the bubble (and the absence of liquid). Moreover, the '715 patent teaches that the energy of the first bubble initiation pulse be sufficient enough to initiate the formation of a vapor bubble. The bubble thus formed may then displace a substantial portion of the fluid medium between a tip of a laser fiber and a target tissue.

The period of time between the first and second pulses can be calculated and then established based on the expected expansion rate of the bubble and the actual distance from the laser fiber tip or light guide to the target tissue. Once a bubble is generated, there are factors which control its spontaneous expansion and a second treatment pulse is then fired, according to the '715 patent, prior the bubble collapse. Van Leeuwen teaches in the prior art ("Non-contact Tissue Ablation by Holmium:YSGG Laser Pulses in Blood," *Lasers in Surgery and Medicine*, Vol 11, 1991) that the bubble will expand to a diameter of about 1 mm in 100 microseconds and to 2 mm in 200 microseconds. Therefore, the '715 teaches a period shorter than 200 microseconds between the bubble initiation pulse and the following treatment pulse.

The bubble initiation pulse, based on the '715 patent, preferably is shorter than 50 microseconds and preferably shorter than 30 microseconds. In an example discussed in the '715 patent, providing a Holmium treatment laser and using a 0.5 mm fiber diameter, the bubble initiation pulse should be at least 0.02 joules—the energy required to boil water with 2.1 micron laser at the tip of the fiber. The bubble initiation pulse consumes, according to this example, 2% of 1 joule treatment pulse.

U.S. Pat. No. 5,632,739 teaches that a delay between a bubble initiation pulse and a treatment pulse is chosen so that the second pulse is emitted when the bubble size and corresponding amount of displaced fluid is at its maximum extent.

However, presently much of the pulse energy remains absorbed by the water or other biological liquid on its way to the target tissue. Non-optimal fiber end-target tissue distance may greatly affect and in fact reduce the efficiency of treatment.

The prior art, however, fails to teach a way to control and optimize the bubble expansion phase by defining, adjusting and optimizing the first initiation pulse delivered by a laser system as a function of a specific set of parameters defining a specific working envelop—total pulse energy chosen by a user for the treatment, treatment pulse repetition rate, fiber diameter and working distance from the tip of the fiber or wave guide to a target tissue and laser type. In addition, the prior art fails to teach an optimization process for determining the delay between the initiation and treatment pulses. It is one aspect of the present invention to address these shortcomings in the prior art.

Included in the solution is the optimization of treatment parameters to shape and modulate the laser pulse to provide a more effective laser-tissue interaction. This may involve optimization of pulse energy, pulse energy level(s), the number of pulses, the type and size of fiber used, and the distance of the fiber tip to the target tissue. Two pulses may be utilized so that the second pulse travels inside the bubble formed by the first of the pulses. Thus, the timing of the second pulse and any delay between the first and the second pulses may provide further optimization benefits. Further, the optimization may work in a "closed loop" mode so that the various controllable parameters can be controlled and changed on the fly to provide the most effective treatment.

SUMMARY OF THE PRESENT INVENTION

In an aspect, a method of optimizing the irradiation of a target with laser radiation, wherein the laser radiation is associated with a laser radiation delivery device and the laser radiation is delivered to the target by one of a waveguide or an optical fiber, the waveguide and the optical fiber each having a distal delivery end, wherein the distal delivery end is spaced from the target, wherein the space between the distal delivery end of the guide and the target is occupied by a liquid medium, and wherein the laser radiation is delivered along a light path in at least one train of laser pulses of a wavelength which is at least partially absorbed in the liquid medium, the at least one train of pulses having a first laser pulse and a second laser pulse. The method includes the steps of: selecting and mounting on the laser radiation delivery device a waveguide or optical fiber type to be used in irradiating the target; then, selecting at least the following parameters: selecting the total energy of the at least one train of pulses to be delivered to the target, and selecting the distance from the distal delivery end to the target; the method further includes providing a controller which controls the laser radiation delivery device and implements the steps of selecting the total energy delivered by the laser radiation delivery device and selecting the distance from the distal delivery end to the target; the method further includes initiating irradiation of the target for the at least one train of pulses by generating the first laser pulse with sufficient energy ($E^i$) to form a vapor bubble in the liquid medium at the distal delivery end; allowing the vapor bubble formed to expand an amount sufficient to displace a substantial portion of the liquid medium from the space between the distal delivery end and the target; thereafter, after the selected time delay ($T^d$) sufficient for the formed vapor bubble to reach its optimum extent, generating the second laser pulse ($E^p$), the second laser pulse being delivered to the target through the formed vapor bubble, thereby minimizing the laser radiation absorbed by the liquid medium and optimizing the laser radiation reaching the target. The controller further includes a memory including a lookup table, the lookup table including a plurality of parameters including $E^i$, $E^p$ and $T^d$, and wherein the steps of selecting the waveguide or optical fiber type, selecting the total energy to be irradiated and selecting the distance from the distal delivery end to the target causes the controller to access the lookup table to select corresponding parameters for $E^i$, $E^p$ and $T^d$ and to cause the delivery device to generate and deliver laser radiation with the selected parameters for $E^i$, $E^p$ and $T^d$.

In another aspect, the ratio of $E^i/E^p$ is from 10:1 to 1:10, the at least one train of pulses comprises two pulses or greater than two pulses. The at least one train of pulses may be more than one train of pulses and the step of selecting comprises the further step of selecting a repetition rate for delivery of the more than one train of pulses.

In yet another aspect, the method further includes the steps of: measuring the actual energy irradiated by the laser; comparing the actual measured energy to the total selected energy; and, if the comparison demonstrates variance of the actual measured energy from the selected total energy, adjusting one or more of the selected parameters for any following train of pulses to achieve the selected energy delivered to the target. The target may be a tissue, an organ or a formed stone within a human body.

In a further aspect, the lookup table comprises one or more datasets containing optimized values of $E^i$, $E^p$ and $T^d$ for a plurality of waveguide or optical fiber types and distances from the distal delivery end to the target, and the step of selecting a waveguide or optical fiber type causes the controller to access the lookup table to determine the optimal values of $E^i$, $E^p$ and $T^d$.

In yet a further aspect, the type of waveguide or optical fiber type includes at least one of the parameters of: fiber diameter, fiber material, fiber numerical aperture and shape of the distal delivery end.

In an aspect, the step of selecting the distance from the distal delivery end to the target includes the further step of measuring the distance and selecting the measured distance. Further, the step of measuring the actual energy delivered by the laser is performed by a photodetector in the light path of the laser radiation. The step of adjusting the one or more parameters is accomplished by a closed loop feedback circuit operatively connected to the programmable controller.

In another aspect, the step of selecting the waveguide or optical fiber type includes the further step of mounting the waveguide or optical fiber onto the delivery device, and wherein the device automatically recognizes the parameters of the waveguide or optical fiber. Further, the step of automatically recognizing is performed by a RFID identification tag mounted on the delivery device and on the waveguide or optical fiber.

In yet a further aspect, the programmable controller indicates on a user interface associated with the programmable controller whether or not the waveguide of optical fiber type is compatible with the one or more parameter selected. Further, the at least one train of pulses includes one or more of: more than one $E^i$ and more than one $E^p$.

In another aspect, the controller controls the laser radiation delivery device and implements the steps of selecting the total energy delivered by the laser radiation delivery device and selecting the distance from the distal delivery end to the target based on the waveguide or optical fiber type mounted on the delivery device.

In an aspect, a method of irradiating a target with laser radiation, wherein said radiation is delivered to the target by a guide having a delivery end, and wherein the delivery end is spaced from the target, and wherein the space between the delivery end of the guide and the target is occupied with a liquid medium, and wherein the laser radiation has a wavelength which is absorbed in the liquid medium, The method comprising the steps of: generating a first laser pulse having sufficient energy to form a vapor bubble in the liquid medium at the delivery end of the guide; and, generating a second laser pulse a predetermined time after the first laser pulse, said predetermined time being selected to allow the vapor bubble to expand an amount sufficient to displace a substantial portion of the liquid medium from the space between the delivery end of the guide and the target so that said second laser pulse may be delivered to the target through the vapor bubble thereby minimizing the laser radiation absorbed by the liquid medium and maximizing the laser radiation reaching the target.

In another aspect, in a medical laser system for treating tissue with a laser beam, in which the tissue being immersed in a liquid medium formed primarily of water, the system includes: a solid state gain medium generating an output wavelength between 1.0 and 10.6 microns; a flashlamp for exciting the gain medium to generate a laser beam; an optical fiber for guiding the laser beam from the gain medium to the tissue, said fiber having a delivery end positioned close to but spaced from the tissue to be treated; and a controller for controlling the flashlamp and functioning to sequentially generate a series of first and second laser pulses, wherein each said first laser pulse has an energy sufficient to form a vapor bubble in the liquid medium at the delivery end of the fiber and wherein each said second laser pulse is generated a predetermined time after the first laser pulse, said predetermined time being selected to allow the vapor bubble created by the first laser pulse to expand an amount sufficient to displace a substantial portion of the liquid medium from the space between the delivery end of the fiber and the tissue so that said second laser pulse may be delivered to the tissue through the vapor bubble thereby minimizing the laser radiation absorbed by the liquid medium and maximizing the laser radiation reaching the target.

BRIEF DESCRIPTION OF THE DRAWINGS

FIG. 4 is a matrix illustrating the relationships of parameters for a 200 micron fiber.

FIGS. 5A and 5B and 6A and 6B illustrate respectively optimization distances in relation to power output and fiber size.

FIGS. 11B through 11G illustrate experimental results of the operation of the device of FIG. 11A.

DETAILED DESCRIPTION OF THE PRESENT INVENTION

According to one aspect of the present invention, after the firing of a first initiation pulse, a second treatment pulse is fired only after a bubble is generated by the first initiation pulse and only after the bubble has reached its maximal size.

Figure 1A:
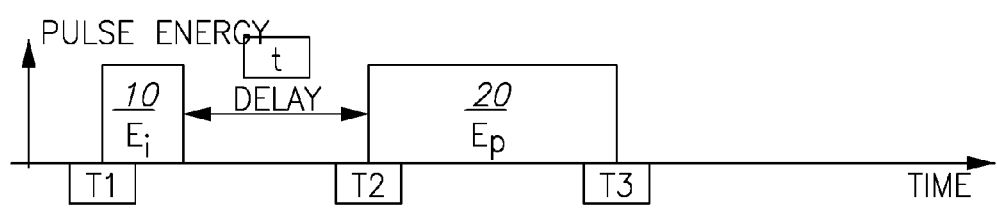
FIGS. 1A, 1B and 1C illustrate in principle the differences between regular (1C) and double pulses (1A and 1B).
Figure 1B:
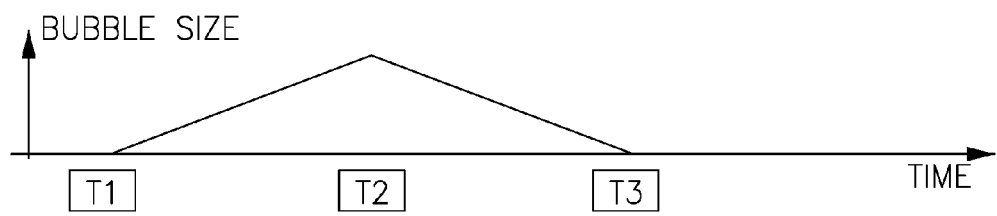

Referring now to FIGS. 1A and 1B, these figures are directed to the amount of the pulse energy over time (FIG. 1A) and to the size of the bubble formed over time (FIG. 1B). A first initiation pulse 10 is fired at T1 followed by a second treatment pulse 20 fired at T2 after a delay of t. The initiation pulse is characterized by energy $E_i$ and treatment pulse is characterized by energy $E_t$. Absorbed energy $E_i$ in the liquid medium located between the tip of the fiber to the target tissue creates a bubble in a short delay after T1. This bubble expands and reaches its nearly maximum size at around time T2. According to this aspect of the present invention, a second treatment pulse is fired only at a time point close to T2, around the time the bubble size is about its maximum size.

It should be mentioned that the real optimization point is also, among other things, dependent upon the total pulse energy, the pulse repetition rate, the fiber type and the fiber tip-to-target tissue distance. According to this aspect of the invention, after time T2, the bubble begins to shrink until it totally collapses at time T3. During the time after T2 when the bubble starts to collapse, a target tissue may experience an attractive force moving it, if feasible (for example if the target was a kidney stone floating in body fluid), towards the energy delivery end of a fiber or a light guide. This same attractive force may further reduce the distance a laser beam travels through the medium until it reaches the target tissue and therefore energy attenuation may be reduced.

Figure 1C:
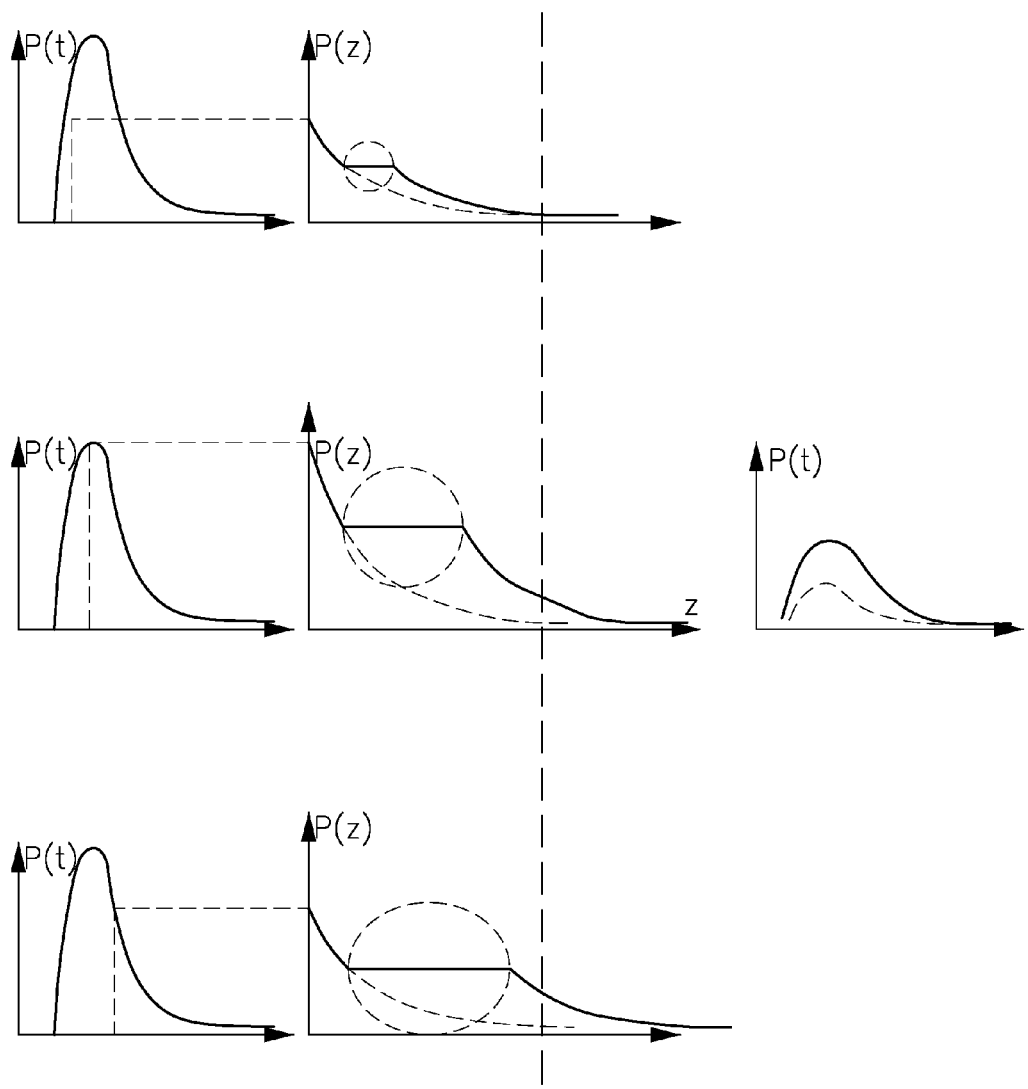

Turning now to FIG. 1C, this figure illustrates holmium laser pulse irradiation in a liquid environment (such as water or physiology solution), resulting in formation of cavitation bubbles. The amount of energy needed for the bubble formation is provided at the expense of the energy delivered to the target, which is a direct energy loss. On the other hand, once being created, the bubble reduces the liquid layer thickness between the fiber tip and a target, which the beam passes through, decreasing its total absorption in water.

This process is schematically shown on the FIG. 1C, in which the left column of figures represents the laser pulse power dependence on time domain P(t) for 3 different phases. The figures in the middle column show how the pulse power is distributed over the distance to the target for the same pulse phases. The circles shown represent the developing bubble. The time dependence of the resulting pulse delivered to the target (compared with that one without the bubble) is shown in the right figure.

Analyzing the above figures from top to bottom it can be observed that the energy level delivered to the target is different for each phase of the pulse, as follows:

In the first row, the pulse is just beginning, its energy is still low as can be seen in the middle graph. The bubble created is still small as well.

In the second row down, the energy of the pulse is at its highest. Therefore, the middle graph also shows higher energy level. The bubble is also much larger, though still not at its maximum due to the time required for its expansion. Within the bubble there is no energy loss, as can be seen by the flat section of the graph.

In the last row, the pulse energy is already declining, however the bubble size is at its maximum, and therefore the energy delivered to the target is still significant.

Based on the above explanation, the right column of the graph shows the theoretical energy delivered to the target, taking the bubble effect into consideration (the solid line), and without taking it into consideration (dashed line). It can be seen that the actual energy delivered is higher because of the creation and the presence of the bubble.

It is clearly seen that the bubble formation, to a certain extent, improves the pulse propagation through the liquid environment. A main aspect of the present invention is to optimize the process to get as much power on the target tissue or stone as possible.

One potential way of accomplishing this goal is a special pulse modulation, in which the pulse energy is delivered to a target in two different parts separated by a certain interval of time. An added value is due to the fact that inertial movement of the liquid surrounding the opening bubble (during the mentioned interval of time) occurs without additional energy loss. By varying the ratio of two parts' energies into which the pulse is divided, and the time interval between them, the optimal energy delivery conditions can be obtained.

One of the challenges during a laser treatment is to keep the target tissue in place once it absorbs the optical energy. In certain cases, the target tissue may have a degree of freedom to move in a direction which pushes it away from the tip of the fiber. This may happen, for example, when the target is a stone in the urinary track to be treated, as mentioned above. The optical energy absorbed by the stone may be transformed, at least partially, into kinetic energy which pushes the stone in a direction away from the tip of the fiber. This phenomenon is known to those skilled in the art as retropulsion. In the context of this invention, retropulsion means that the distance the laser light beam must travel from the tip of the fiber to the target tissue may increase. Increased laser light beam traveling distance may mean increased energy loss due to absorption and scattering in the surrounding media. Therefore, according to another aspect of the invention, a treatment energy pulse may be fired during a period the bubble is collapsing to reduce retropulsion of a target tissue and at the same time improve target stone ablation.

In general, in laser systems the pulse energy produced by a laser depends on multiple factors. Among these factors are laser efficiency, which may vary between one cavity to another, and may vary as a function of the working temperature or as a function of the pumping energy. Each factor may also vary in time. These variances may well affect the timing and extent of bubble formation vis a vis the initiation and the treatment pulses. In order to overcome the resulting pulse energy fluctuations, a closed loop control system described herein may implemented as another aspect of the invention. The closed loop control system may be required in order to assure that energy level of each bubble initiation pulse is within a specific predefined range of energies, so that bubble size and expansion rate can be predicted.

Therefore, according to this aspect of the present invention, a system is configured to measure the pulse energy, compare the measured pulse energy to a predefined energy level and to feedback in a closed feedback loop the pumping energy source to compensate on the fly for incorrectly-energized pulses to assure that the level of each bubble initiating pulse is within a predefined range of values.

Figure 2:
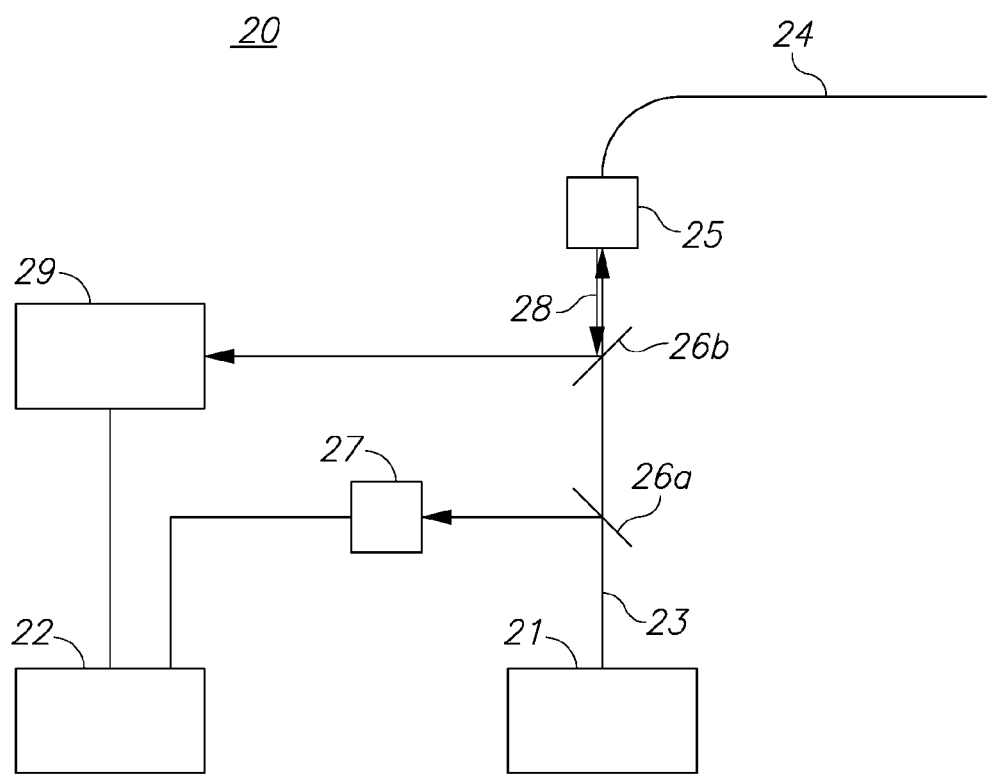
FIG. 2 illustrates in a schematic fashion one embodiment of a device of the present invention.

Referring now to FIG. 2, this figure illustrates schematically one embodiment of the present invention. Laser system 20 consists of a laser module 21 and a control unit 22. A laser beam 23 exiting laser module 21 is configured to reach an optical wave guide 24 through connector 25. Partially transparent mirror 26a located along the optical path of beam 23 and is configured to reflect, at least a portion of beam 23 into photodetector module 27. Some of the backscattered light from a target tissue enters wave guide 24 and passes through connector 25, is configured to target partially transferred mirror 26b and enter into module 29. Module 29 is configured to measure the distance between the tip of waveguide 24 and a target tissue. Modules 27 and 29 are also controlled by programmable controller 22. During operation, programmable controller unit 22 receives a first electrical signal from module 27 indicative of the energy level of the laser pulse, whether Ei or Et, and a second electrical signal from distance measurement module 29 indicative to a distance change between the tip of waveguide 24 and a target tissue. Laser system 20, based on at least one of the first and second indicative signals, is configured to adjust the amount of the current supplied to the laser pumping element to keep energy levels Ei and Et within the parameters which were chosen by a user and in accordance with any dynamic change in the laser performance or the distance to a target tissue.

Figure 3A:
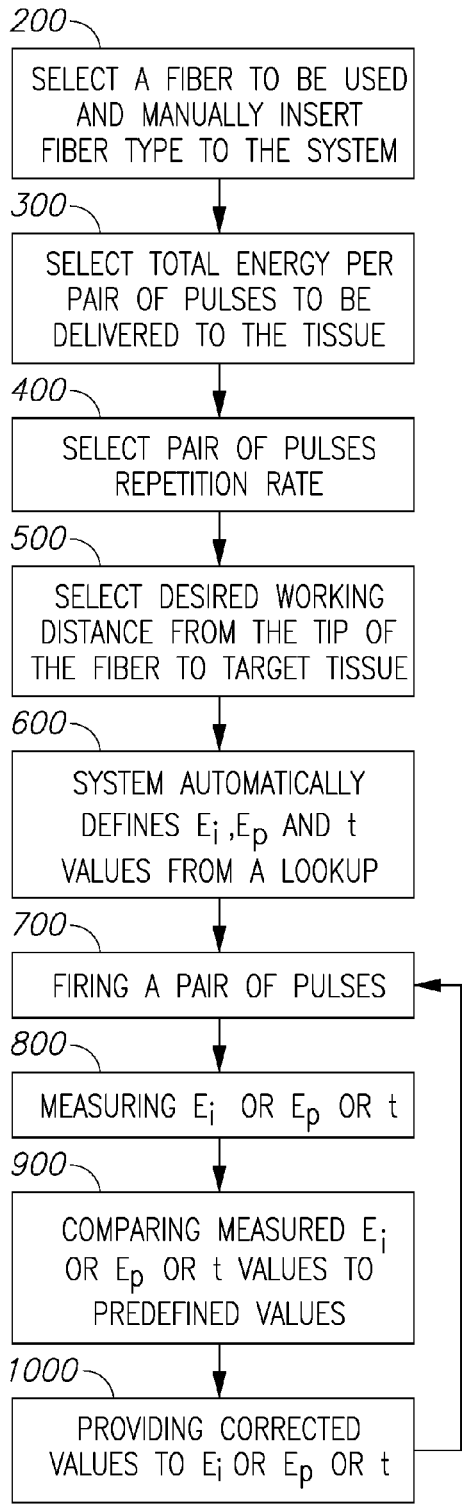
FIGS. 3A and 3B are flowcharts illustrating the operation of the device of FIG. 2 in the present invention.
Figure 3B:
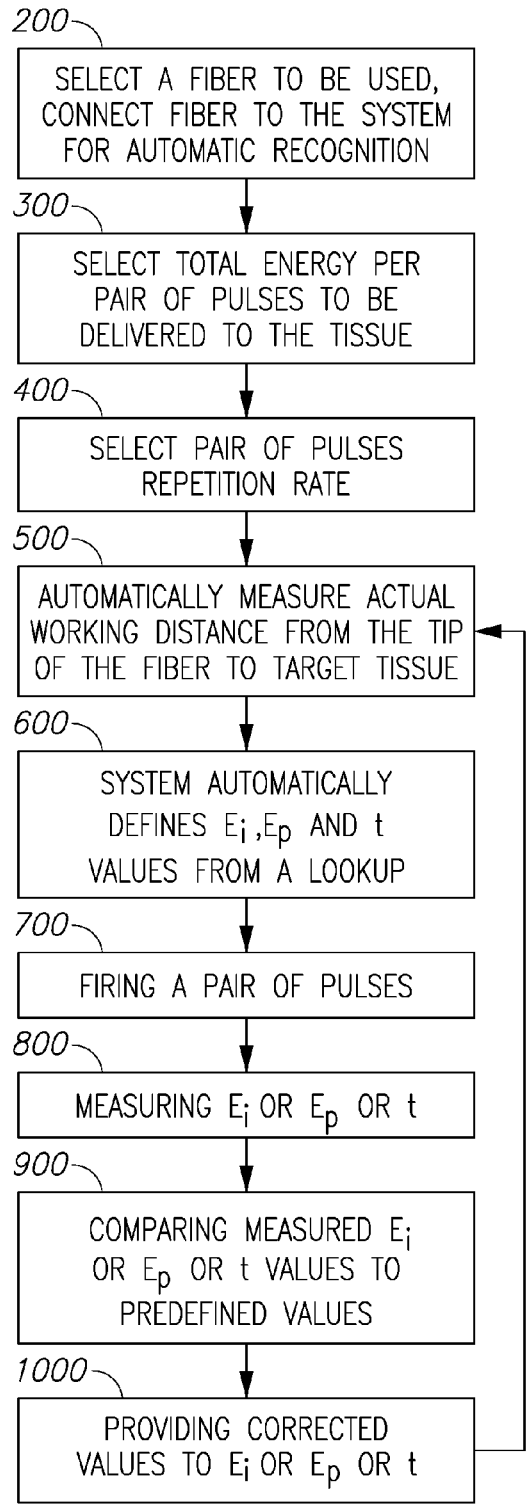

FIGS. 3A and 3B are flow diagrams showing the operation of the laser system of FIG. 2 which is configured to optimize the double pulse regime discussed above. The double pulse regime of the present invention may also be referred to as a "B-pulse" in the present specification and disclosure. In stage 200, a user selects the type of fiber in use. According to embodiment described in FIG. 3A, a user may select manually a type of fiber to be used in the treatment. Alternatively, as shown in FIG. 3B, an automatic fiber recognition system may be implemented. In stage 300, a user selects the required treatment energy level. The pulse energy defined by the user for the treatment may be the overall energy expected to be emitted by the laser system in the pair of the initiation and the treatment pulses. In other words, and as will be discussed below, the system may be programmed and configured, using a suitable programmable controller, to set up a double pulse mode in a way transparent to the user. The user in this embodiment is not required to set up the values of $E_i$ and t.

In stage 400, a user selects the pulse repetition rate. It should be mentioned that in this context the pulse repetition rate, from the standpoint of the user, is the repetition rate between a pair of pulses. Each pair of pulses contains an initiation pulse and a treatment pulse. In stage 500, according to FIG. 3A, a user selects the desired (average) working distance between the tip of the fiber and the target tissue.

According to another embodiment of the present invention, as shown in FIG. 3B, the working distance may be detected by the system automatically, for example, by using a distance evaluation technology as described in the U.S. patent application Ser. No. 13/811,926, owned by the same assignee as the present invention, the entirety of which is incorporated herein by reference. In stage 600, based on previously manually loaded or automatically detected parameters, the system defines automatically, from a lookup table operatively associated with the programmable controller or calculates the working values for a double pulse regime, the energy required for the bubble initiation pulse $E_i$, the energy for treatment pulse $E_p$ and time duration t for the delay until a treatment pulse is fired once the initiation pulse is terminated.

It may be mentioned here that $E^i$ may be a single pulse which is configured to initiate a single bubble in the liquid media between the tip of the fiber and the target tissue. According to another embodiment, $E^i$ may be a sequence of two or more pulses. A second Ei pulse may cross the first bubble and generate a second bubble once it exits the first bubble and hits again a liquid media. Multiple $E^i$ pulses may create, in this way, a chain of multiple bubbles. Therefore, according to this aspect of the invention, the distance between the tip of a fiber and a target tissue may be spanned with more than one bubble in order to reduce the absorption level of the liquid media. The time sequence for practicing multiple $E^i$ pulses, according to another aspect of the invention, should be optimized in such a way that a next $E^i$ pulse is fired while the bubble initiated by a previous $E^i$ pulse still exists and has not yet been totally collapsed.

In stage 700, the treatment laser fires a pair of pulses at the target tissue. The system may be configured to measure actual values of each pulse. In stage 800 and in stage 900, the system is configured to compare the measured values to the predefined values on stage 600. Should the measured parameters deviate from the predefined parameter, the system automatically corrects such deviation in stage 1000 and a new set of working parameters are sent to the programmable controller which then causes to be initiated the next pair of pulses in stage 700. In this way, the system maintains the actual working values within the predefined range. It should be understood that during stage 800, the system may be configured to measure different parameters which may be related to actual laser pulse energy.

For example, according to one embodiment, the system may use a photodetector which is configured to measure optical energy output of $E_i$, $E_p$ or the total pulse energy. According to another embodiment, for example, the system may be configured to measure current or voltage pulses which are sent to the laser pumping energy source. Therefore, the feedback loop may be configured to feedback, based on each measured parameter, whether this is a measured optical value, a measured current or voltage value or any other measured parameter which is related to a pulse energy.

Referring now to FIG. 4, this chart shows one exemplary set of optimized double pulse parameters for one specific fiber sold by the applicant herein, Lumenis Ltd. of Israel, called SlimLine 200, having a core size diameter of 272 microns. According to this example, the set of parameters shows optimized set of double pulse parameters for this specific fiber for a desired working distance of 1 mm. It should be mentioned that a typical set of parameters, having different values obviously, will characterize different fibers and/or different desired working distances. The left side column on the table lists possible working energies in Joules as emitted from the tip of the fiber and as can be selected by a user through the manipulation of a user interface operatively associated with the system. Again, this number reflects the total energy of a pair of pulses, as mentioned above. The upper row of the table lists possible repetition rates as can be selected by a user in the system's user interface. As can be seen, for every combination of energy and repetition rate there is a set of two parameters: $E_i$ and t. In this table, $E_i$ is given in Joules as delivered to the pumping energy—to the lamp. Therefore, as one example, if a user chooses to work at 0.6 joule with a repetition rate of 20 Hz, then the system will automatically define $E_i$ at 23 joule and t at 200 microseconds. The contents of the chart of this FIG. 4 may be programmed into a lookup table such as that mentioned above. Different tables may be developed for different lasers, different fibers, etc.

Referring now to FIGS. 5A and 5B, shown are examples of optimized set of double pulse modes for two different working distances for a 365 micron fiber and a common working envelope of 1 Joule at 70 Hz. It can be seen in FIG. 5A that at a working distance of about 1 mm, the difference in energy reaching the target tissue in a regular pulse mode (R-pulse) and under a double pulse mode, reaches a maximum level (line 40). This double pulse optimized level is characterized by a set of two parameters $E_i$ and t which are the optimized values for this specific working conditions. In this example, $E_i$=29 J pumping energy and t=220 msec. A similar set of data describing optimized points as shown in FIG. 4 lies behind the graphs shown in FIGS. 5 and 6. In FIG. 5B, shown is the optimized point of $E_i$ and t, for the same 365 micron fiber operating under the same working envelop of 1 joule and 70 Hz but at a distance of about 1.5 mm (line 41). In this example Ei=35 J pumping energy and t=250 msec.

Referring now to FIGS. 6A and 6B, shown are examples of the optimized set of double pulse parameters, (lines 50 and 51), for two different fibers working under the same working envelop and at the same working distance of about 2 mm. The double pulse values for these two different fibers are different.

Figure 7:
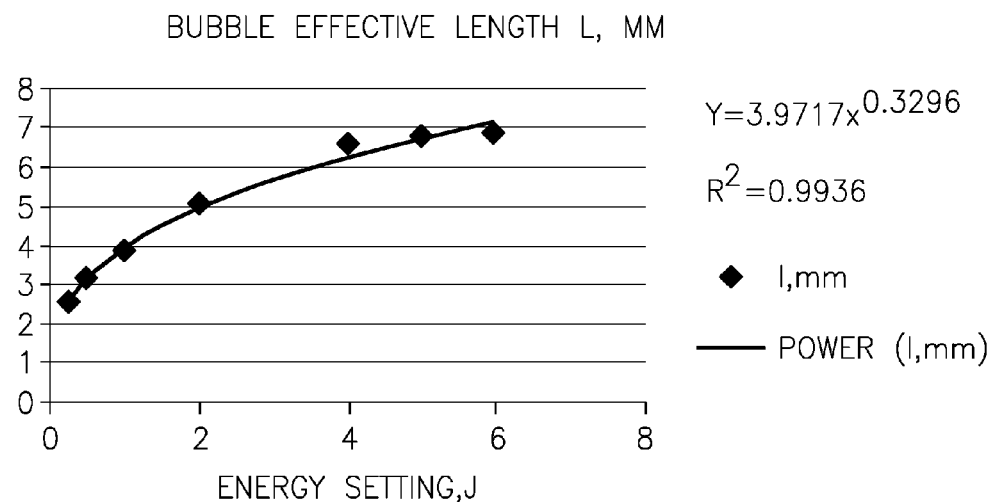
FIG. 7 is a graph illustrating the relationship between bubble length and power output.

Turning now to FIG. 7, this figure shows a graph of the effective bubble length versus the energy setting for a side-firing laser source. The curve shown in FIG. 7 demonstrates that the bubble size dependence on the pulse energy tends to be saturated. Thus, as shown, the energy rise from 4 J to 6 J does not significantly change the length of the bubble formed. Further, the effect of bubble separation from the fiber tip at the end of a pulse as well limits the amount of energy delivered to the target tissue.

The time of bubble expansion and collapse is believed to be substantially determined by the laws of hydrodynamics. When the duration of a high energy pulse becomes longer than the bubble "lifetime", the pulse rest energy was found to create a new bubble. This new bubble is separated from the first, collapsing, bubble. Theoretical consideration (in the limit of sufficiently long, comparing the bubble life and pulses) predicts that the bubble will be expanded in time as about $\sqrt[3]{t}$.

Due to the proportionality between the pulse energy and its duration, the same dependence on energy should be found for the bubble size, about $\sqrt[3]{E}$.

The curve shown in FIG. 7 illustrates that this prediction is in good agreement with the experimental data. Thus, it appears that: (1) the maximum bubble dimension for high energy pulse tends to be saturated at close to 7 mm; (2) when the pulse duration becomes longer that the bubble lifetime, the second bubble which is separated from the first bubble is created. Due to this separation, the energy may well not reach the target tissue; and, (3) experimental curve fits provides about $E^{0.3296}$ dependence between the bubble maximum size and the pulse energy.

While the use of Holmium and Thulium laser sources have been generally discussed above, other combinations of two types of laser cavities have been described as potentially being effective in the provision of pulses to create bubbles in accordance with the present invention. One such arrangement is described in co-pending U.S. provisional application Ser. No. 62/482,335, filed Apr. 6, 2017 and assigned to the same assignee as the assignee of the present invention. The entirety of the disclosure of that application is incorporated by reference herein.

In the above-cited provisional, it is disclosed that while use of a Holmium laser is probably the "gold standard" for the treatment of Benign Prostatic Hyperplasia (BPH), due, among other reasons, to the peak power of a Ho laser source which is 20 times higher than that of a Tm laser, there are as well potential undesirable aspects, including unwanted tissue coagulation and tissue charring.

Given that the Tm wavelength is absorbed in tissue more effectively than a Ho laser, the same or substantially the same results as for a Ho laser may be achieved by providing a pulse duration of 1 ms, which was found to decrease the risk of tissue charring. And, to keep the average power balance the same, it is necessary to increase by the same factor the value of the repetition rate as follows: 20 W=0.5 Kw×1 mS×40 Hz. Thus, the foregoing was found to be a most efficacious treatment regime for tissue applications. The ability to control pulse shape, which is intrinsic to IPG fiber lasers, makes it possible to implement the so-called "Moses" features disclosed in the US patent and US provisional patent application cited above, resulting in improved treatments which take place in a liquid environment in the human body.

As mentioned, one main disadvantage of a Tm fiber laser is that it possesses low peak power (0.5-1.0 Kw for Tm versus 10 Kw for A Ho laser). This results in different laser/tissue interactions. The main two fundamental reasons for the low peak power are:

1. The LED pumping limitations.
2. Small fiber cross section for the Tm fiber laser.

A main disadvantage of a Ho solid state laser is its low efficiency, which is a result of the need for a multistage pumping process (Cr>Tm>Ho). There are energy losses at each stage, resulting in an overall efficiency of less than 4%, versus 15-20% for a Tm fiber laser.

Figure 8:
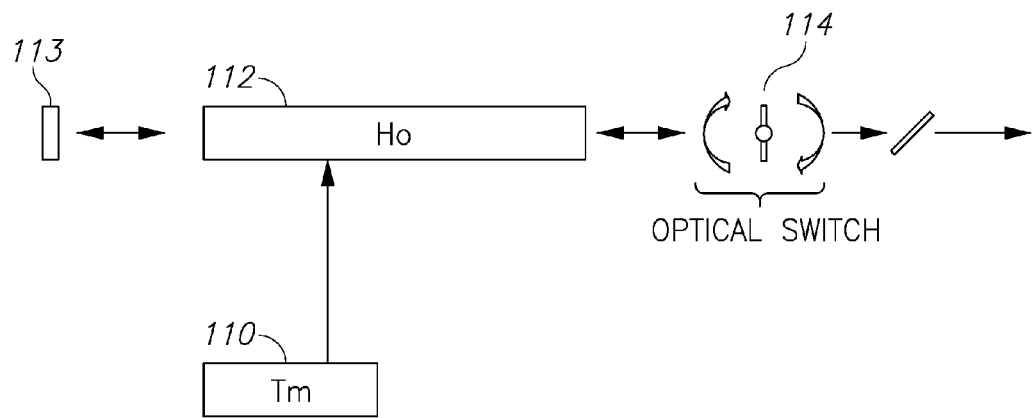
FIGS. 8, 9, and 10 illustrate schematic diagrams of embodiments of Ho and Tm laser cavities in the present invention.

According to an embodiment of the invention for producing a high peak power Holmium laser cavity and for increasing its efficiency, there is provided a CTH pumped solid state Holmium laser cavity as shown in FIG. 8. Tm element 110 is configured to pump Holmium laser rod 112 which is located between a back mirror 113 and an optical switch 114. Optical switch 114 may be any opto-mechanical switch or an opto-electronic device. Opto-mechanical solutions may be based on any rotating or moving optical element. A rotating prism or mirror are only two non-limiting example of possible opto-mechanical switches. A Q-switch module is only one example of an opto-electronic switch. The luminescence decay time for the pumping CTH YAG crystal is about 10 milliseconds, which is at least an order of magnitude longer than that of a Ho laser pulse duration. Therefore, suppressing the laser generation process, for at least part of the time of the pump process, will allow the accumulation of inverse electrons population in the Holmium crystal which are needed to obtain a high peak power pulse. The generation suppression may be accomplished, by way of example, by means of an active Q-switch module or even a mechanically rotating mirror, prism or any other optical moving or rotating element.

As seen in the FIG. 1, rotating mirror 114 may be configured to allow the laser generation process when rotating mirror 114 is about parallel to mirror 113 and about orthogonal to laser rod 112. Optical switch 14 may therefore be in one of two states. In a first On state, the Holmium cavity is configured to amplify and release a laser beam out of the cavity. In a second Off state, the Holmium cavity is configured to block laser amplification and release. The On and Off durations of the Holmium laser cavity may be controlled by optical switch 114. A rotating mirror may be controlled by the system's programmable controller to define On and Off times, for example, based on an angular speed of the mirror. According to another example, rotating mirror may be controlled by a step motor. Such a step motor may switch the mirror from at least one On position to at least one or more Off positions. During Off positions of optical switch 114, pumping energy may be accumulated in Holmium laser rod 112. During On positions of optical switch 114 laser beam may be amplified in the cavity and released from the cavity.

Figure 9:
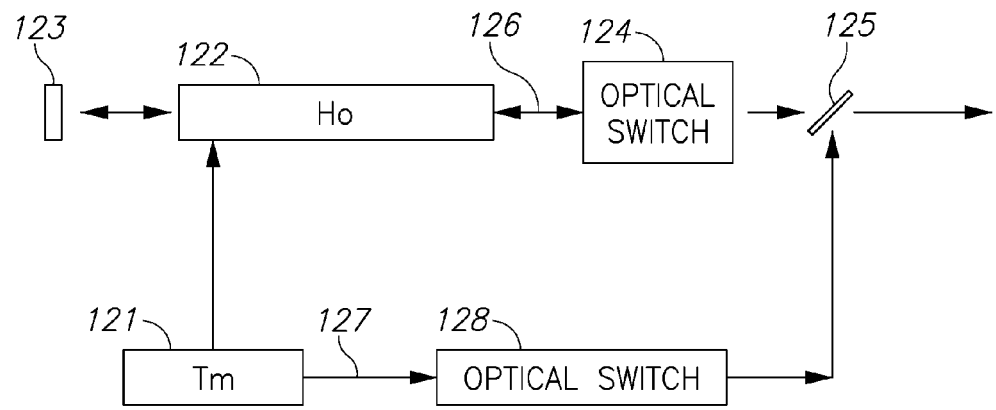

According to another embodiment of the invention for producing a high peak power Holmium laser cavity and for utilizing the multiple pulses technology described in the relevant incorporated references, there is provided a direct Thulium pumped solid state Holmium laser cavity as shown in FIG. 9. Using a Tm fiber laser source for direct pumping of a Ho solid state laser will likely lead to a significant increase in efficiency. According to an embodiment, a fiber Thulium laser cavity 121 is configured to directly pump Holmium laser rod 122 which is located between a back cavity mirror 123 and an optical switch 124 in the front. The On and Off mechanism of the Holmium laser cavity in this embodiment is similar to that mentioned above for the other embodiment shown in FIG. 8. Mirror 125 is configured to be transparent to Holmium laser beam 126 exiting the Holmium laser cavity and at the same time to reflect, in the case fold, Thulium laser beam 127 coming from pumping Thulium laser module 121. A second optical switch 128 along the optical path of the Tm laser 121 is configured to synchronize between one or more Tm bubble initiation pulses and the followed by Holmium treatment pulse. As mentioned above, the absorption of Thulium laser in liquid is stronger than that of Holmium. In order to improve the Moses effect and the inventions disclosed in the relevant incorporated references, a Thulium laser may be used as one or more bubble initiating and/or controlling pulses followed by a Holmium laser treating pulse.

Figure 10:
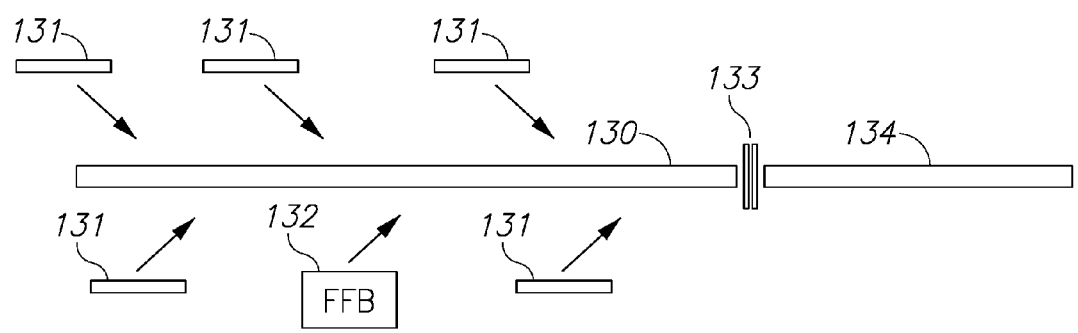

Referring now to FIG. 10, fiber laser 130 is configured to be pumped by at least one pumping element 131 which are optically coupled along and into fiber laser 130. Connector 133 is configured to connect a light guide 134 to deliver the laser energy toward a target tissue. As disclosed in the relevant incorporated references, back scattered light may be collected by wave guide 134 from a target tissue area and be delivered into a fiber integrity module or a tissue distance estimation module (FFB). Therefore, according to this embodiment, at least one FFB module 132 may be optically coupled to fiber laser 30, in a similar way pumping modules 131 are optically connected to laser fiber 130, to allow the realization of these referenced invention in this case of a fiber laser.

Thus, it can be seen that use of one of the setups shown in any of FIG. 8, 9 or 10 as disclosed in the above provisional application can result in improved bubble formation and bubble integrity.

EXAMPLE

Figure 11A:
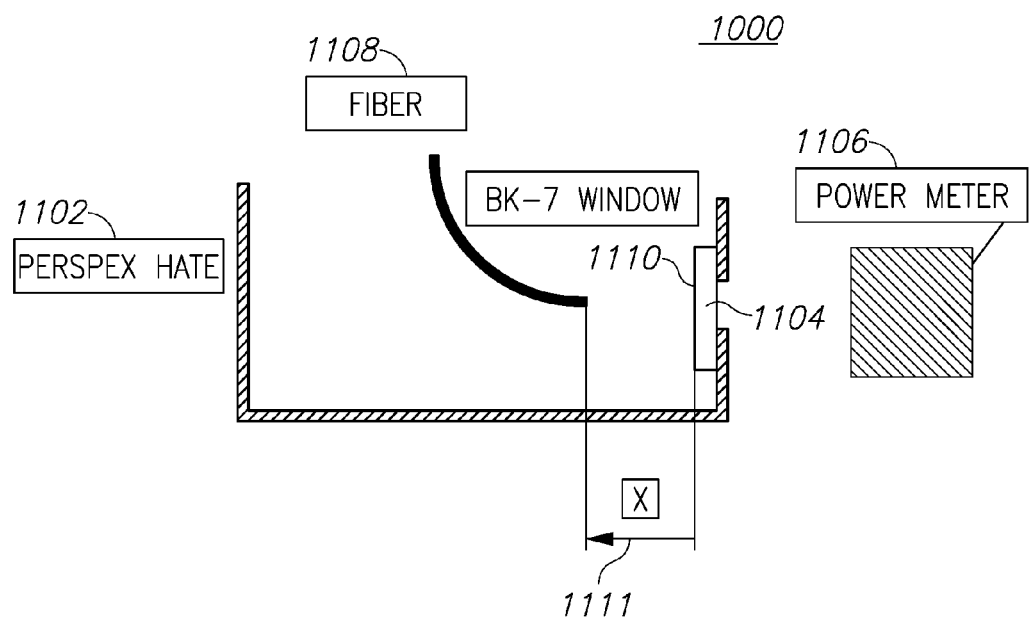
FIG. 11A illustrates an experimental testbed example of the operation of a device demonstrating the present invention.
Figure 11B:
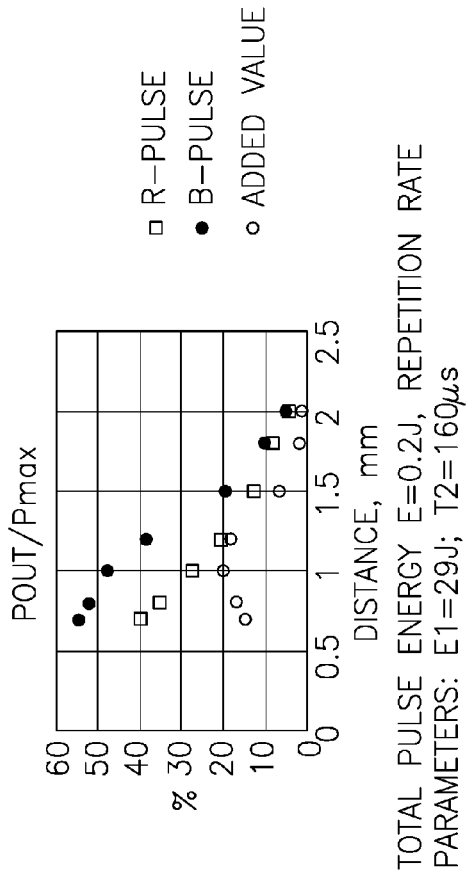
Figure 11B:
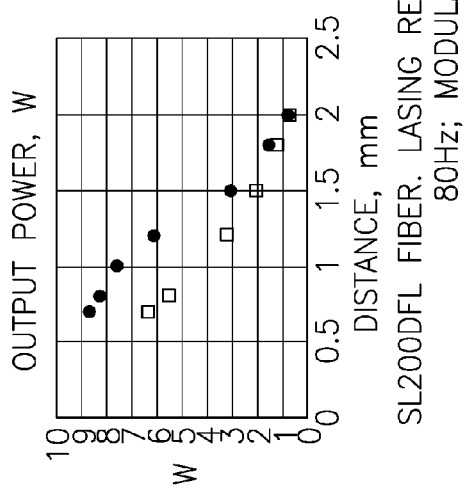
Figure 11C:
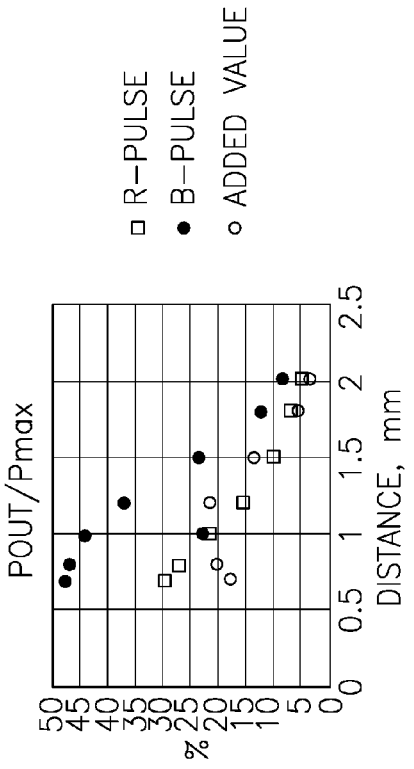
Figure 11C:
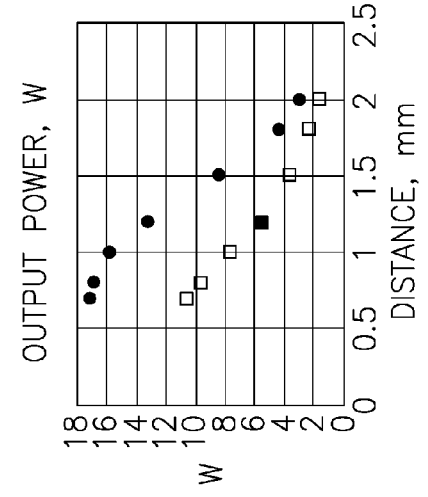
Figure 11F:
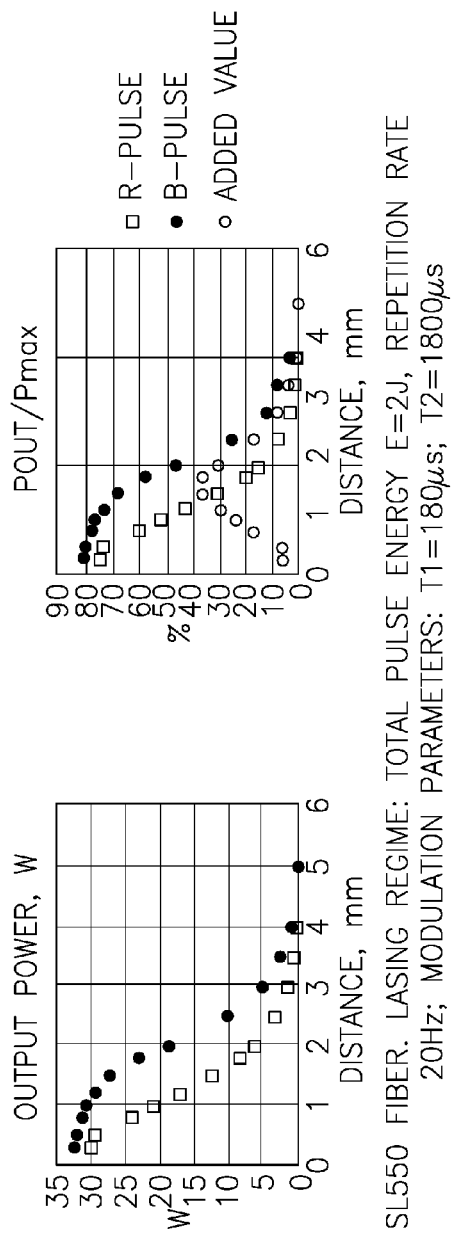
Figure 11G:
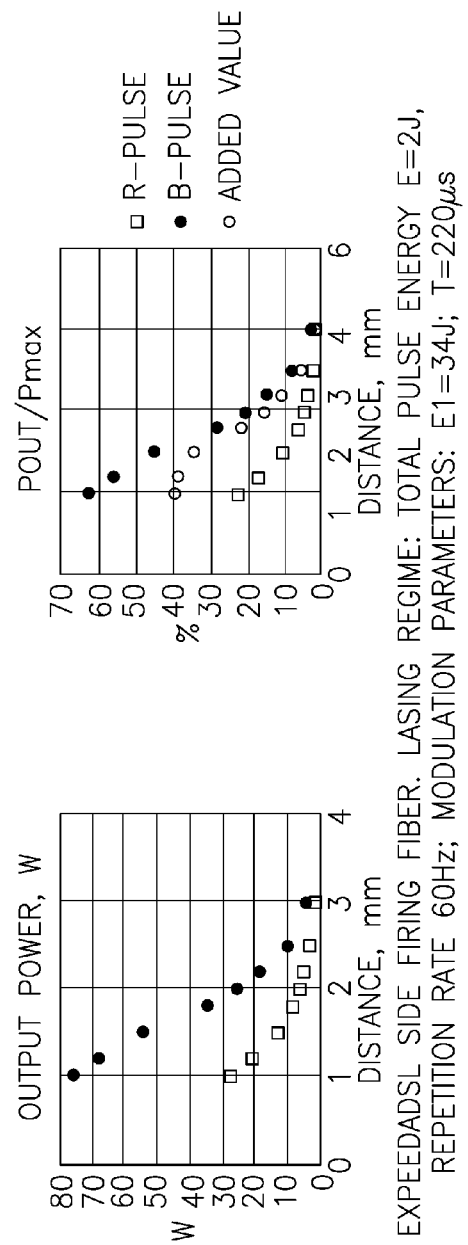

FIG. 11A illustrates an experimental setup to test the operation of a device in accordance with the present invention and FIGS. 11B through 11B the result of the experiments.

The test of the experimental setup of FIG. 11A was performed using specially designed jig 1100 which is shown on the FIG. 11A. This jig makes possible to simulate the real pulse propagation through a water layer to the target.

The bath 1102 with a window 1104, which is transparent to the Holmium wavelength, is filled with water and placed in front of power meter. The fiber 1108 under the test can be precisely moved to control the distance 1111 between the fiber tip and the window glass surface 1110. The measured power value simulates the amount of energy actually delivered to the target (the inner glass surface) for a given distance and laser setting. This way pulses of different modulation parameters can be compared with each other.

The different sets of modulation parameters were found, depending on the average distance, which a surgeon keeps during the operation. Three distances were used for determining the optimal parameters: 3 mm, 2 mm and 1 mm.

To make sure that the features of the present invention are reliable and stable, the power delivered to the target was measured as a function of a distance to the fiber tip for a given set of modulation parameters, for a given lasing regime and for a given fiber.

In the Table 1 below are presented all fibers and laser regimes for which the power-distance dependence was measured.

TABLE 1

List of fibers and measured lasing regimes
Table1

| J/Hz | 5 | 10 | 15 | 20 | 30 | 40 | 60 | 70 | 80 |
|---|---|---|---|---|---|---|---|---|---|
| 0.2 | | | | 2, 1 | | 2, 1 | 2, 1 | | 3, 2, 4, 1 |
| 0.3 | | | | 2, 1 | | 2, 1 | 2, 1 | | 3, 2, 4, 1 |

TABLE 1-continued

List of fibers and measured lasing regimes
Table1

| J/Hz | 5 | 10 | 15 | 20 | 30 | 40 | 60 | 70 | 80 |
|---|---|---|---|---|---|---|---|---|---|
| 0.4 | | | | 2, 1 | | 2, 1 | 2, 1 | | 3, 2, 4, 1 |
| 0.5 | | 2 | | 2, 1 | | 2, 1 | 2, 1 | | 3, 2, 4, 1 |
| 0.6 | | 2 | | 2, 1 | | 2, 1 | 2, 1 | | 3, 2, 4, 1 |
| 0.8 | 2, 1 | 2, 1 | 2, 1 | 2, 1 | | | | | 3, 2, 4 |
| 1 | 3, 2, 1 | 3, 2, 1 | 3, 2, 1 | 3, 2, 4, 1 | 5 | 3, 2 | 3, 2, 5 | 3, 2 | |
| 1.2 | | | | | | | | 3, 2, 1 | |
| 1.5 | | | | 3 | | 3, 2, 1 | 3 | | |
| 2 | | | | 3, 2, 4, 1 | 5 | 3, 4 | 3, 5 | | |
| 3 | | | | 3, 2, 4 | | | | | |
| 3.5 | | | 3 | 3, 4 | 3 | | | | |
| 4 | | 3, 4 | | 3 | | | | | |
| 5 | | 3, 4 | | 3 | | | | | |
| 6 | 3, 4 | 3, 4 | | | | | | | |

1 - SL200D/F/L
2 - SL200
3 - SL365
4 - SL550
5 - Expeeda

FIGS. 11B through 11G show the dependence of power delivered to the target on the distance to the fiber tip. These are the typical curves; all others look similar differing only quantitatively. Because the graphs were taken from different SW versions, sometimes the pairs of modulation parameters are T1, T2 (pump pulse duration and time interval accordingly) and sometimes—E1, T2 (pump pulse energy and time interval).

The percentage scale on the graphs is referring to the laser setting. For example (FIG. 3), from the distance of 1 mm the regular pulse delivers to the target 27% of the 0.2 J*80 Hz=16 W set power while the B-pulse—47%

The window used in this experiment did not allow the measurement at a very close distance. It is more important for thin fibers, because the cavitation bubbles become more destructive. That's why the range of distances to a target was limited to few tenths of mm.

In some graphs "Added value" is the difference between the B-Pulse and the regular modes.

All the power vs. distance graphs that have been collected show that this dependence has so-called "cigar" shape.

This means that there is no significant difference between regular and B-pulse at the distance range edges. When the fiber tip is very close to the target the role of the bubble becomes minor, and therefore the energy delivered to the target is the same. When the distance exceeds approximately 3-3.5 mm the amount of energy delivered to the target becomes insignificant even for the strongest (5-6 J) pulses. This means that, again, there is no difference between B-pulse and regular pulses, as the delivered energy is negligible.

The most difference (always in favor of B-pulse) occurs at that distance where modulation parameters are optimized. It means that, once the preferable working distance is determined, the optimization can be done for that point. It should be noticed that decreasing the distance for which the optimization is done results in decreased advantage of B-pulse over the regular pulses (the "cigar" shape becomes thinner).

As the so-called Moses effect or feature (increase in an energy delivery to a target) is caused by the formation of a bubble, it is seen that the effect strongly depends on the fiber size, which determines the power density. That is the reason each fiber type requires special optimization of the laser pulse modulation parameters.

What is claimed is:

1. A method of optimizing the irradiation of a target tissue contained in and mobile within a body lumen with laser radiation, wherein the laser radiation is associated with a laser radiation delivery device and the laser radiation is delivered to the target tissue by one of a waveguide or an optical fiber, the waveguide and the optical fiber each having a distal delivery end, wherein the distal delivery end is spaced from the target tissue, wherein the space between the distal delivery end of the guide and the target tissue is occupied by a liquid medium, and wherein the laser radiation is delivered along a light path in at least one train of laser pulses of a wavelength which is at least partially absorbed in the liquid medium, the at least one train of pulses having a first laser pulse and a second laser pulse, both pulses being substantially along the same longitudinal axis, said method comprising the steps of:

selecting and mounting on the laser radiation delivery device a waveguide or optical fiber type to be used in irradiating the target tissue;

selecting at least the following parameters: selecting the total energy of the at least one train of pulses to be delivered to the target tissue, and selecting the distance from the distal delivery end to the target tissue;

further comprising a controller which controls the laser radiation delivery device and implements the steps of selecting the total energy delivered by the laser radiation delivery device and selecting the distance from the distal delivery end to the target tissue;

initiating irradiation of the target tissue for the at least one train of pulses by generating the first laser pulse along the longitudinal axis with sufficient energy ($E^i$) to form a vapor bubble in the liquid medium at the distal delivery end;

allowing the vapor bubble formed to expand an amount sufficient to displace a substantial portion of the liquid medium from the space between the distal delivery end and the target tissue;

thereafter, after the selected time delay ($T^d$) sufficient for the formed vapor bubble to have reached its optimum extent and begun to collapse, generating the second laser pulse ($E^p$), the second laser pulse being delivered along the longitudinal axis to the target tissue through the formed vapor bubble, thereby minimizing the laser radiation absorbed by the liquid medium and optimizing the laser radiation reaching the target tissue;

whereby the collapsing bubble causes the target tissue to remain substantially stationary when the second laser pulse is delivered, thus reducing retropulsion of the target tissue;

the controller further comprising a memory including a lookup table, the lookup table including a plurality of parameters including $E^i$, $E^p$ and $T^d$, and wherein the steps of selecting the waveguide or optical fiber type, selecting the total energy to be irradiated and selecting the distance from the distal delivery end to the target causes the controller to access the lookup table to select corresponding parameters for $E^i$, $E^p$ and $T^d$ and to cause the delivery device to generate and deliver laser radiation with the selected parameters for $E^i$, $E^p$ and $T^d$.

2. The method of claim 1, wherein the ratio of $E^i/E^p$ is from 10:1 to 1:10.

3. The method of claim 1, wherein the at least one train of pulses comprises two pulses.

4. The method of claim 1, wherein the at least one train of pulses comprises greater than two pulses.

5. The method of claim 1, wherein the at least one train of pulses is more than one train of pulses and the step of selecting comprises the further step of selecting a repetition rate for delivery of the more than one train of pulses.

6. The method of claim 5, further comprising the steps of: measuring the actual energy irradiated by the laser; comparing the actual measured energy to the total selected energy; and, if the comparison demonstrates variance of the actual measured energy from the selected total energy, adjusting one or more of the selected parameters for any following train of pulses to achieve the selected energy delivered to the target tissue.

7. The method of claim 6, wherein the step of measuring the actual energy delivered by the laser is performed by a photodetector in the light path of the laser radiation.

8. The method of claim 6, wherein the step of adjusting the one or more parameters is accomplished by a closed loop feedback circuit operatively connected to the controller.

9. The method of claim 1, wherein the target tissue is a tissue, an organ or a formed stone within a human body.

10. The method of claim 1, wherein the lookup table comprises one or more datasets containing optimized values of $E^i$, $E^p$ and $T^d$ for a plurality of waveguide or optical fiber types and distances from the distal delivery end to the target tissue, and wherein the step of selecting a waveguide or optical fiber type causes the controller to access the lookup table to determine the optimal values of $E^i$, $E^p$ and $T^d$.

11. The method of claim 1, wherein the type of waveguide or optical fiber type includes at least one of the parameters of: fiber diameter, fiber material, fiber numerical aperture and shape of the distal delivery end.

12. The method of claim 11, wherein the controller indicates on a user interface associated with the controller if the waveguide of optical fiber type is compatible with the one or more parameter selected.

13. The method of claim 1, wherein the step of selecting the distance from the distal delivery end to the target tissue includes the further step of measuring the distance and selecting the measured distance.

14. The method of claim 1, wherein the at least one train of pulses includes one or more of: more than one $E^i$ and more than one $E^p$.

15. The method of claim 1, wherein the controller controls the laser radiation delivery device and implements the steps of selecting the total energy delivered by the laser radiation delivery device and selecting the distance from the distal delivery end to the target tissue based on the waveguide or optical fiber type mounted on the delivery device.

16. A method of optimizing the irradiation of a target tissue contained in and mobile within a body lumen with laser radiation, wherein the laser radiation is associated with a laser radiation delivery device and the laser radiation is delivered to the target tissue by one of a waveguide or an optical fiber, the waveguide and the optical fiber each having a distal delivery end, wherein the distal delivery end is spaced from the target tissue, wherein the space between the distal delivery end of the guide and the target tissue is occupied by a liquid medium, and wherein the laser radiation is delivered along a light path in at least one train of laser pulses of a wavelength which is at least partially absorbed in the liquid medium, the at least one train of pulses having a first laser pulse and a second laser pulse, both pulses being substantially along the same longitudinal axis, said method comprising the steps of:

selecting and mounting on the laser radiation delivery device a waveguide or optical fiber type to be used in irradiating the target tissue;

selecting at least the following parameters: selecting the total energy of the at least one train of pulses to be delivered to the target tissue, and selecting the distance from the distal delivery end to the target tissue;

further comprising a controller which controls the laser radiation delivery device and implements the steps of selecting the total energy delivered by the laser radiation delivery device and selecting the distance from the distal delivery end to the target tissue;

initiating irradiation of the target tissue for the at least one train of pulses by generating the first laser pulse along the longitudinal axis with sufficient energy ($E^i$) to form a vapor bubble in the liquid medium at the distal delivery end;

allowing the vapor bubble formed to expand an amount sufficient to displace a substantial portion of the liquid medium from the space between the distal delivery end and the target tissue;

thereafter, after the selected time delay ($T^d$) sufficient for the formed vapor bubble to have reached its optimum extent and begun to collapse, generating the second laser pulse ($E^p$), the second laser pulse being delivered along the longitudinal axis to the target tissue through the formed vapor bubble, thereby minimizing the laser radiation absorbed by the liquid medium and optimizing the laser radiation reaching the target tissue;

whereby the collapsing bubble causes the target tissue to remain substantially stationary when the second laser pulse is delivered, thus reducing retropulsion of the target tissue;

the controller further comprising a memory including a lookup table, the lookup table including a plurality of parameters including $E^i$, $E^p$ and $T^d$, and wherein the steps of selecting the waveguide or optical fiber type, selecting the total energy to be irradiated and selecting the distance from the distal delivery end to the target causes the controller to access the lookup table to select corresponding parameters for $E^i$, $E^p$ and $T^d$ and to cause the delivery device to generate and deliver laser radiation with the selected parameters for $E^i$, $E^p$ and $T^d$; and, wherein the step of selecting the waveguide or optical fiber type includes the further step of mounting the waveguide or optical fiber onto the delivery device, and wherein the device automatically recognizes the parameters of the waveguide or optical fiber.

17. The method of claim 16, wherein the step of automatically recognizing is performed by a RFID identification tag mounted on the delivery device and on the waveguide or optical fiber.

18. A medical laser system for treating a tissue portion with a laser beam, said tissue portion being mobile and immersed in a liquid medium formed primarily of water within a body lumen, said system comprising:
- a solid-state gain medium generating an output wavelength between 1.0 and 10.6 microns;
- a flashlamp for exciting the gain medium to generate a laser beam;
- an optical fiber for guiding the laser beam from the gain medium to the tissue portion, said fiber having a delivery end positioned close to but spaced from the tissue portion to be treated; and
- a controller for controlling the flashlamp and functioning to sequentially generate a series of first and second laser pulses, wherein each said first laser pulse and each said second laser pulse being substantially along the same longitudinal axis, and wherein each said first laser pulse has an energy sufficient to form a vapor bubble in the liquid medium at the delivery end of the fiber and wherein each said second laser pulse is generated a predetermined time after the first laser pulse, said predetermined time being selected to allow the vapor bubble created by the first laser pulse to expand an amount sufficient to displace a substantial portion of the liquid medium from the space between the delivery end of the fiber and the tissue portion wherein the controller controls the initiation of said second laser pulse such that it is delayed a period of time so that it may be delivered to the tissue through the vapor bubble after the vapor bubble has reached its maximum extent and has begun to collapse, thereby minimizing the laser radiation absorbed by the liquid medium and maximizing the laser radiation reaching the target and whereby the collapsing bubble causes the tissue portion to remain substantially stationary when the second laser pulse is delivered, thus reducing retropulsion of the tissue portion.

\* \* \* \* \*